United States Patent [19]
Rose et al.

[11] Patent Number: 6,090,346
[45] Date of Patent: Jul. 18, 2000

[54] STERILIZATION USING ULTRAVIOLET LIGHT AND ULTRASONIC WAVES

[75] Inventors: Edward V. Rose; William E. Clark, Jr., both of Folsom, Calif.

[73] Assignee: Spectrum Environmental Technologies, Inc., Citrus Heights, Calif.

[21] Appl. No.: 08/999,273

[22] Filed: Dec. 29, 1997

[51] Int. Cl.[7] .............................. A61L 2/10; A61L 2/025
[52] U.S. Cl. ................... 422/20; 422/24; 422/128
[58] Field of Search .................. 422/20, 23, 24, 422/128

[56] References Cited

U.S. PATENT DOCUMENTS

| | | |
|---|---|---|
| 2,249,473 | 7/1941 | Jackson et al. . |
| 2,814,081 | 11/1957 | Stevenson . |
| 3,481,687 | 12/1969 | Fishman . |
| 4,448,750 | 5/1984 | Fuesting ................................. 422/20 |
| 5,074,322 | 12/1991 | Jaw . |
| 5,216,251 | 6/1993 | Matschke . |
| 5,330,722 | 7/1994 | Pick et al. ............................. 422/121 |
| 5,449,502 | 9/1995 | Igusa et al. . |
| 5,466,425 | 11/1995 | Adams ................................. 422/20 X |
| 5,601,786 | 2/1997 | Monagan ............................. 422/108 |
| 5,658,530 | 8/1997 | Dunn . |
| 5,688,475 | 11/1997 | Duthie, Jr. .......................... 422/186.3 |

FOREIGN PATENT DOCUMENTS

| | | |
|---|---|---|
| 0 083 448 | 7/1983 | European Pat. Off. . |
| 0 673 656 | 9/1995 | European Pat. Off. . |
| 2269275 | 12/1975 | France . |
| 2 599 255 | 12/1987 | France . |
| 35 00 487 | 10/1986 | Germany . |
| 469009 | 2/1952 | Italy . |
| 671922 | 5/1952 | United Kingdom . |
| 2 040 150 | 8/1980 | United Kingdom . |
| WO 91 10455 | 8/1991 | WIPO . |

OTHER PUBLICATIONS

Certified Translation of DE 35 00 477 A1 Prepared By Legal Language Services and dated Aug. 25, 1999.

*Primary Examiner*—Elizabeth McKane
*Attorney, Agent, or Firm*—John P. O'Banion

[57] ABSTRACT

A sterilization method for organic or inorganic matter which combines exposure to ultraviolet light and ultrasonic waves. The ultrasound waves are applied "dry" in that the object is not immersed into a liquid solution during the exposure cycle. This makes the sterilization method suitable for use in a mass production assembly line setting. Exposure of the object to the ultraviolet light and ultrasound waves can occur simultaneously, sequentially, or in alternating fashion.

10 Claims, 3 Drawing Sheets

STERILIZATION USING ULTRAVIOLET LIGHT AND ULTRASONIC WAVES

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to sterilization methods, and more particularly, to a method and apparatus for sterilizing organic and inorganic matter in a non-liquid environment using a combination of ultraviolet light and ultrasonic waves.

2. Description of the Background Art

The effective removal of viable pathogenic microorganisms is essential to those who regularly come into contact with potentially infectious microorganisms. Medical care givers, such as physicians, nurses, emergency medical technicians, and dental care givers, such as dentists and oral hygienists, are frequently exposed to bodily fluids which may contain infectious microorganisms, such as viruses, bacteria, etc. Instrumentation (including human hands) must be effectively sterilized to prevent the transmission of potentially infectious microorganisms between patients and to the workers themselves. Microbiological researchers are constantly handling potentially infectious microorganisms as a regular part of their responsibilities and require effective and frequent sterilization of instrumentation and hands to protect themselves and their co-workers from such undesirable exposure.

People working in the field of food processing, packaging and service also have an essential need for the effective removal of potentially infectious microorganisms from a variety of food surfaces and the various equipment used in handling and processing. As part of their jobs, these workers are required to handle a variety of raw meats, poultry, seafood, baked goods, and vegetables for processing, packaging, delivery and sale to the general public. Food service workers are required to handle and prepare food products that are often to be consumed shortly thereafter by the public. Raw meats, poultry and seafood, especially, are ideal sources for the incubation and multiplication of undesired and potentially infectious microorganisms. The workers' equipment and hands must be effectively sterilized on a frequent basis to prevent infecting themselves or spreading microorganisms from a contaminated source to the rest of the supply, and thus subjecting the general public to the risk of exposure.

Similarly, there is a need for effective removal of potentially infectious microorganisms from a variety of medical and dental instruments and devices that cannot be effectively sterilized by other conventional means such as autoclaving due to their internal electronic nature. These instruments and/or devices are often used on patients where infectious microorganisms that are present on the surface of the instruments and/or devices may be transmitted onto (or even into) the patient being treated if not effectively sterilized prior to its intended use, which can cause potentially life threatening conditions.

Food products available for public consumption also require effective removal of potentially dangerous microorganisms prior to consumption by the general public. As discussed above, handling of food products by workers with non-sterilized hands can result in the spread of undesired microorganisms, or conversely, direct contact of food products with contaminated food processing and packaging equipment can also result in the spread of unwanted microorganisms.

A commonly used method for sterilizing the hands of medical, dental and food service workers is repeated washing and/or scrubbing of the hands. This procedure can be time consuming as it must be repeated frequently after the worker comes into contact with a potentially contaminated source. Also, this method may not effectively sterilize the worker's hands due to ineffective washing techniques, types of cleaning agents used, or even the length of time spent physically cleaning the hands. Constant, repetitive hand washing can also damage the skin due to use of soaps, detergents and the actual scrubbing actions that remove the skin's natural oils and can leave the skin dehydrated and irritated. The disadvantages of excessive time consumption, non-thorough hand sterilization, and skin irritation may cause the worker to avoid the frequent hand washing required to effectively prevent the spread of potentially infectious microorganisms.

Medical and dental instruments and devices are commonly sterilized via use of steam autoclaves and other methods that incorporate the use of heat, steam, gamma radiation, electron beam, and/or chemical agents to remove viable pathogenic microorganisms. However, the effectiveness of these methods varies and they typically require the use of expensive, sophisticated equipment and generally involve a substantial amount of time to complete. Also, some instruments and devices are particularly sensitive to high temperatures, moisture, gamma radiation, electron beams and/or certain chemicals being used, and cannot survive these methods of sterilization. Therefore these instruments, in particular, require other methods of sterilization.

The use of ultraviolet light is another method used to sterilize organic and inorganic matter. Exposure to certain ultraviolet light band wavelengths has been discovered to be an effective means of destroying microorganisms. In using this method of sterilization, the user places the object or device to be cleaned into a chamber to expose the device or object to be cleaned to a prescribed dose of ultraviolet light. The interior of the cleaning chamber is usually coated with a reflective surface which reflects the light to ensure that all surfaces of the object being sterilized are irradiated with a sufficient amount of the ultraviolet light. The amount of time required for an adequate dosage of the ultraviolet light varies but typically requires at least ten seconds. However, the use of ultraviolet light for microbiological sterilization of organic and inorganic surface matter has historically been abandoned in favor of more sophisticated methods that employ heat, steam, gamma radiation, electron beams, and/or chemicals. This may be a result of manufacturers' desire to offer more expensive sterilization devices in lieu of simplified technology. Typically, the use of ultraviolet light has been relegated to the treatment of air and/or water, which is generally circulated past the ultraviolet light source in a cabinet or the like and then into the sterilization environment.

Other sterilization methods involve the use of ultrasonic waves which resonate through an aqueous solution in which the item to be sterilized is immersed either partially or completely. The ultrasonic waves within the aqueous solution cause zones of compression and vacuity which act physically on the object placed within the aqueous solution causing foreign substances thereon to be dislodged and dispersed within the solution. When the object to be sterilized is a human hand, for example, the aqueous solution employed must be compatible with human skin, thus limiting the types of available aqueous solutions which can be used and which are effective. Furthermore, because the hands have to be immersed into an aqueous solution to utilize this sterilization method, the hands become saturated with the aqueous solution and must thereafter be dried off. The hand drying process usually entails convecting air over the skin surface for a period of time until the hands are sufficiently dry. This consumes time and may even leave the skin dehydrated. If the item to be sterilized is some other organic material, such as meats, poultry, seafood or vegetables, immersing the item into an aqueous solution can damage or even destroy its properties, thus rendering the food product useless. Similarly, certain medical instruments and devices that need sterilizing become inoperable when they are immersed in an aqueous solution. These instances illustrate the need for a sterilization method which can effectively, frequently, and quickly sterilize organic and inorganic matter in a non-aqueous environment.

There are also sterilization methods which combine the use of both ultraviolet light and ultrasonic waves; however the ultrasonic emitting step is performed in an aqueous solution. Using this method, an ultraviolet light source is positioned to irradiate a cleaning liquid in a cleaning tank into which the item to be sterilized is immersed. A piezo-electric transducer agitates the liquid ultrasonically causing both microscopic and macroscopic agitation, which dislodges foreign substances from the surface of the item. Because the ultraviolet irradiating step occurs concurrently with the ultrasonic process, the microorganisms dislodged from the item being sterilized is subjected to the ultraviolet light, thereby destroying the microorganisms. In these combination methods, the disadvantages associated with each step previously mentioned still exist.

Therefore a need exists for a method to sterilize organic and inorganic material in a non-liquid environment using a combination of ultraviolet light and ultrasonic waves. The present invention satisfies those needs, as well as others, and overcomes the deficiencies in prior technology.

BRIEF SUMMARY OF THE INVENTION

The present invention overcomes the disadvantages discussed regarding currently known and employed sterilization methods and achieves the stated objectives. Accordingly, the present invention comprises a method for sterilizing organic and inorganic materials which uses a combination of ultraviolet irradiation and an ultrasonic emission, with the combination sterilization method being performed in a non-liquid environment. The invention does not require the use of a liquid to contact the object being exposed to the ultrasonic waves. Instead, the simultaneous combination of ultraviolet light and ultrasonic waves provides for effective sterilization of items without having to place the item in a water or other liquid solution during exposure to the ultrasonic waves. The ultrasound waves are applied "dry" in that the object is not immersed into a liquid solution during the exposure cycle. The ultraviolet light is emitted onto the surface of the material to be sterilized at wavelengths which will destroy viable pathogenic microorganisms subjected to a variable time duration sufficient to ensure complete destruction of microorganisms exposed to the ultraviolet light. The ultrasonic waves cause excitation and oscillation three-dimensionally on all exposed surfaces of the item being sterilized which enable microorganisms attached thereto that are not molecularly bonded to the surface of the object to become dislodged from the surface of the object and momentarily airborne, thereby subjecting the dislodged microorganisms to greater surface area exposure to the ultraviolet light energy than would otherwise occur if the microorganism were still attached to the surface. The ultraviolet irradiating and ultrasonic excitation steps occur simultaneously to produce the desired effect of increased sterilization efficiency. Upon sufficient exposure time to the combined energy sources, the object is then removed from the chamber in a sterilized condition.

The combination ultraviolet and ultrasonic sterilization method of the present invention can be implemented for mass sterilization of items produced on assembly lines. Because this sterilization method operates in a non-liquid environment, the ultraviolet light source and ultrasonic emitter assembly can be placed along the path of a moving conveyor belt. As the mass produced items move along the conveyor belt, all available exterior surfaces of each item exposed to the energy sources are irradiated by the ultraviolet light from the ultraviolet light source and ultrasonic waves from the ultrasonic emitter. The ultraviolet light irradiation step occurs with the ultrasonic wave emission process, thus creating a single exposure event necessary to produce the desired sterilization effect. The items then continue along their path on the conveyor belt in a sterilized condition.

Mass-produced food items such as meats, poultry, seafood and vegetables can be sterilized using this combination method without affecting the taste or texture of the food items being treated. The ability of the combination sterilization method to perform effective sterilization in a non-liquid environment eliminates the food item from having to be exposed to any liquid whatsoever, which would otherwise generally affect the texture and/or taste of the food item. Since the ultraviolet light is exposed only to the surface of the food item being sterilized and not beneath the surface due to its poor penetrating capabilities, the light will not "cook" or alter the interior of the food item or otherwise affect its taste or texture.

An object of the invention is to provide a quick, efficient and reliable method for effectively eliminating potentially infectious microorganisms from every available exterior surface of either organic or inorganic matter using a simultaneous combination of ultraviolet light and ultrasonic waves.

Another object of the invention is to provide a combination ultraviolet and ultrasonic sterilization method in which the sterilization is performed in a non-liquid environment.

Yet another object of the invention is to provide a method of sterilization which is non-hazardous and safe for the user and those in close proximity to the user.

Yet another object of the invention is to provide a method of sterilization which can be easily implemented to sterilize mass produced items made on an assembly line.

Yet another object of the invention is to provide a method of sterilization which can sterilize food items without affecting the texture and/or taste of the food item.

A further object of the invention is to provide a method of sterilization which is simple to use and which does not require special training or procedures to implement.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
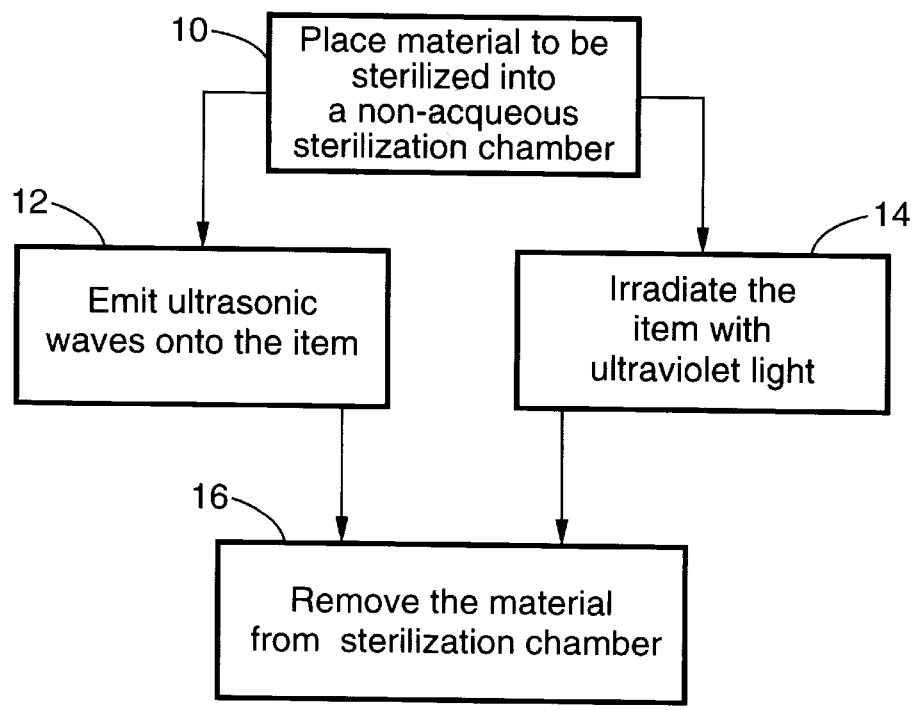
FIG. 1 is a flowchart depicting a general method of sterilizing organic and inorganic material by simultaneous emission of ultrasonic waves and irradiation of ultraviolet light in accordance with the invention.

Referring more specifically to the drawings, for illustrative purposes the present invention is embodied in the method and apparatus generally shown in FIG. 1 through FIG. 4. It will be appreciated that the method may vary as to details of the steps and their sequence and that the apparatus may vary as to the details of its parts without departing from the basic concepts as disclosed herein.

The present invention comprises a method and apparatus for sterilizing organic and inorganic material by simultaneously exposing the material to ultraviolet light and ultrasonic waves in a non-liquid environment. An example of the steps involved in the sterilization method of the present invention can be seen in FIG. 1. At step 10, an object or device to be sterilized is placed into an enclosed sterilization chamber which contains the path of ultraviolet light and ultrasonic waves. At steps 12 and 14, the surface of the material is simultaneously exposed to ultrasonic waves and ultraviolet light for a period of time ranging from approximately two seconds to six minutes, depending on the surface characteristics of the item being sterilized. Note that the being exposed to the ultrasonic waves is not placed in contact with a liquid. Instead, the simultaneous combination of ultraviolet light and ultrasonic waves provides for effective sterilization of items without having to place the item in a water or other liquid solution during exposure to the ultrasonic waves; that is, in a non-liquid or "dry" environment. By exposing the surface of the material to ultrasonic waves at the same time it is exposed to the ultraviolet light, the surface of the material is physically excited during irradiation by the ultraviolet light. This causes agitation and oscillation of bacteria and other undesired organisms on the surface of the material, thereby increasing the amount of surface area exposed to the ultraviolet light. By maintaining the surface of the material in a state of physical excitation while applying the ultraviolet light energy, the ultraviolet light energy will irradiate all available exposed surfaces of the material being sterilized. When sterilization is complete, the material is then removed from the sterilization chamber at step 16.

As can be seen, therefore, the present invention uses ultrasonic waves to agitate and oscillate microorganisms on the surface of the material to be sterilized, thereby increasing the surface area of the microorganism that is exposed to the ultraviolet light. This aids in the destruction of the microorganism. In most instances, an ultraviolet irradiation period of ten seconds to one minute is sufficient, especially for bacterial sterilization. However, sterilization for certain molds and fungi may require additional exposure time. Sterilization time may also depend on the porosity of the surface of the item being sterilized. Generally, the more porous the surface, the greater the sterilization time required. However, with food objects, longer exposure times could affect the color, texture or taste of the object.

In the preferred method, an ultrasonic emitter continuously emits ultrasonic waves while ultraviolet light is cycled on and off to irradiate the surface of the material being sterilized. However, it will be appreciated that the ultrasonic wave emitting step 12 and the ultraviolet light irradiating step 14 can also be performed in a sequential fashion as long as the surface of the material being sterilized is exposed to ultrasonic waves sufficient to cause agitation of microorganisms thereon and/or to produce other potentially desired effects on the surface of the material being treated.

Figure 2:
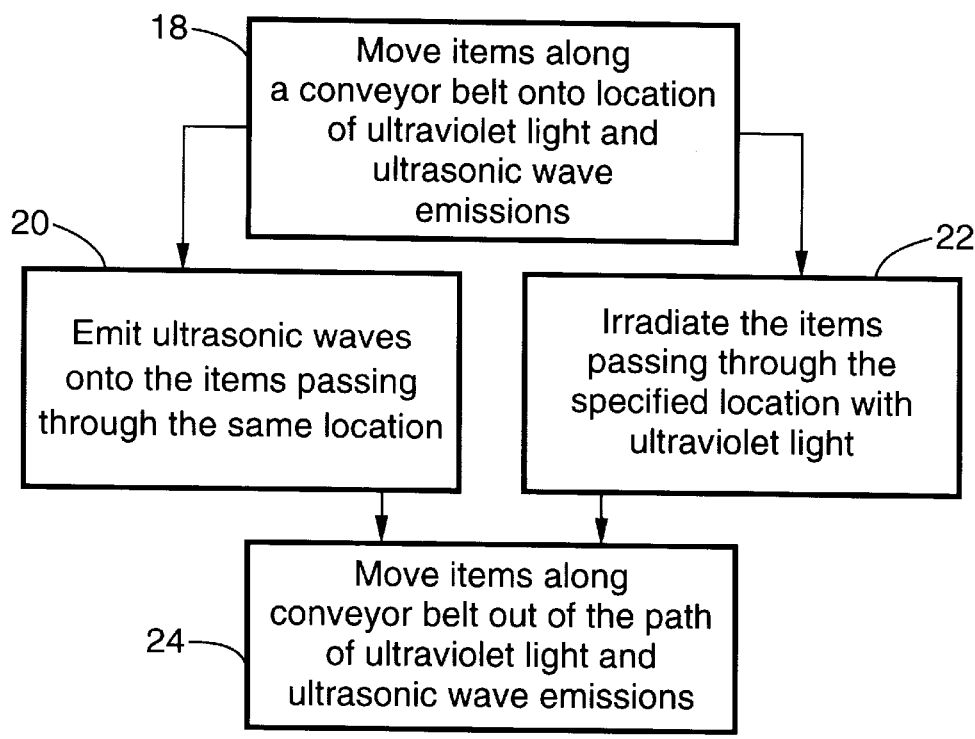
FIG. 2 is a flowchart depicting a general method of sterilizing organic and inorganic material being produced on an assembly line by simultaneous emission of ultrasonic waves and irradiation of ultraviolet light in accordance with the invention.

Referring now to FIG. 2, an example of a specific application of the sterilization method of the present invention to mass produced or bulk items using a conveyor or other transport system can be seen. Because the sterilization method of the present invention is performed non-aqueously, items mass produced along an assembly line or transported along a conveyor belt or other transport device can be sterilized by exposing the assembly line, conveyor belt or the like to ultraviolet light and ultrasonic waves such that the surface of the items moving along the conveyor belt receives at least a minimum exposure to the ultraviolet light and ultrasonic waves. For example, at step 18 the items are moved along a conveyor belt or the like into a location where the items can be exposed to ultraviolet light and ultrasonic waves. The items are then simultaneously exposed to ultrasonic waves and ultraviolet light at steps 20 and 22, respectively, and then moved out of the path of the ultrasonic waves and ultraviolet light at step 24 when exposure is complete. As indicated previously, the ultrasonic wave emitting step 20 and the ultraviolet light irradiating step 22 can also be performed in a sequential fashion as long as the surface of the material is exposed to ultrasonic waves sufficient to cause agitation of microorganisms thereon and/or to produce other potentially desired effects on the surface of the item being treated.

Figure 3:
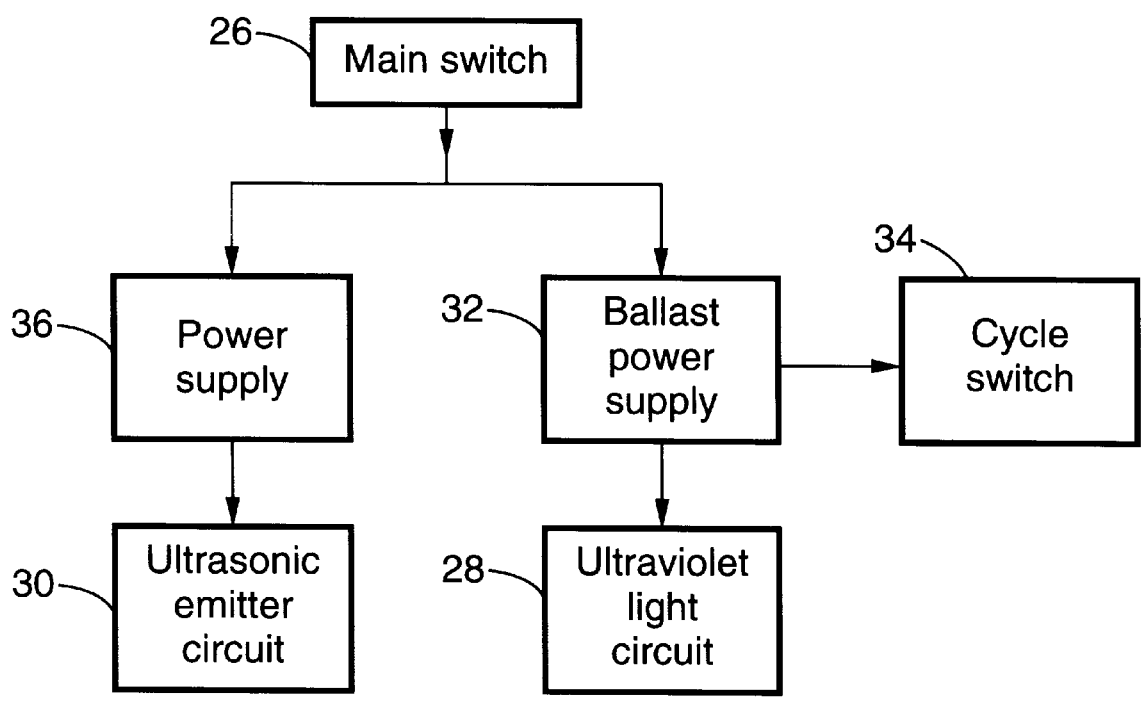
FIG. 3 is a block diagram of a sterilization system used for the method of the invention.

Referring also to FIG. 3, a functional block diagram of a sterilization apparatus in accordance with the present invention is shown in which a main switch 26 controls an ultraviolet light circuit 28 to provide ultraviolet light for the ultraviolet irradiating steps described above and an ultrasonic emitter circuit 30 to provide ultrasonic waves for the ultrasonic emission steps described above. Ceramic piezo-electric transducers (not shown) are preferably used to emit the ultrasonic waves. Ultraviolet light circuit 28 is preferably powered by a ballast power supply 32 which is cycled for activation and deactivation by a cycle switch 34. A conventional power supply 36 powers ultrasonic emitter circuit 30.

Figure 4:
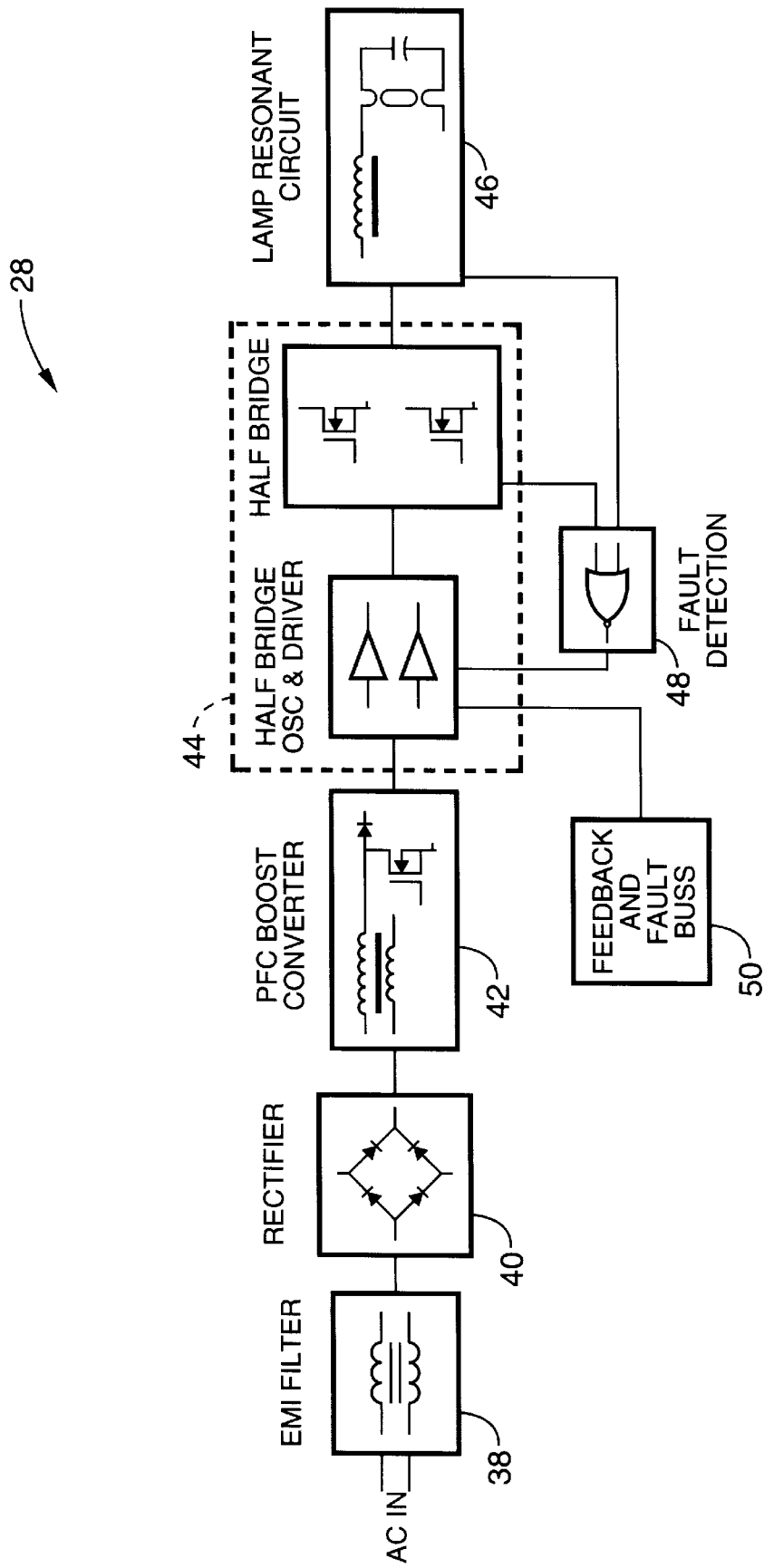
FIG. 4 is a block diagram of an ultraviolet light circuit of the sterilization system shown in FIG. 3.

Referring also to FIG. 4, a functional block diagram of ultraviolet light circuit 28 is shown. Ultraviolet light circuit 28 is preferably a high frequency switching supply operating in the 20 KHz to 50 KHz range, and preferably comprises an EMI filter 38, a rectifier 40, a power factor controller 42, a feedback ballast control circuit 44, an RCL series-parallel lamp resonant output circuit 46, shutdown circuitry 48 and a feedback and fault buss 50. Power factor controller 42 is preferably a boost converter operating in critically continuous, free-running mode. Ballast control section 44 provides frequency modulation control of lamp resonant output circuit 46. Shutdown circuitry 48 utilizes a lamp circuit detection and comparator logic for the safe and smooth turn-off and automatic re-starting. Feedback control and lamp fault buss 50 are isolated from ballast control section 44 by opto-couplers (not shown).

Ballast control section 44 preferably drives four twenty-one watt T5 type lamps (not shown) between a standby mode and a sterilization mode. In the standby mode, the circuit maintains the lamps at an approximate 10% to 20% output level. The relatively low output standby mode enhances lamp life and lowers filament temperature between sterilization cycles, but allows for virtually no heat-up time and instantaneous ionization of the lamps to full output when the circuit is switched from the standby mode to the sterilization mode. Using low pressure mercury vapor lamps, a life cycle of up to 120,000 cycles can be expected from the lamps due to the design of the circuit as compared to 1,500 to 3,000 cycles when using conventional power supplies.

In the present invention, the ultraviolet light is typically emitted at a wavelength between approximately 180 nm to 325 nm, with a preferred wavelength of 254.7 nm for germicidal control, and a power density consistent with that necessary to accomplish sterilization. Typical power densities range from 400,000 to 1,000,000 microwatts per $cm^2$ per second. The ultrasonic waves preferably sweep a range of approximately 20 KHz to 40 KHz in a sawtooth pattern having a cycle period of one second, although a steady 24.7 KHz output frequency has been found to be most effective for destroying microorganisms on human skin, as well as for removing from the surface of the object being sterilized, all non-skinned microorganisms via use of ultrasound where the object is not placed into a solution for agitation by the ultrasonic waves. The ultrasonic output is preferably approximately 119 dB at 0.5 meters with a maximum power output of 5 watts.

Once activated, the ultrasonic emission remains on while the ultraviolet light is cycled as required for sterilization. The ultrasonic emission by itself does not eliminate the microorganisms on the item being sterilized, however, the ultrasonic waves causes the microorganisms to become agitated and begin to oscillate, thereby exposing more surface area of the microorganism to ultraviolet light for irradiation.

Those skilled in the art will appreciate that the invention as described can be implemented using conventional circuitry and that the invention can vary as to configuration and design, including use of analog and digital equivalents for circuit elements. It will also be appreciated that, except as described herein, circuitry to emit ultrasonic waves and ultraviolet light is commercially available and, therefore, is not described in detail herein and does not form a part of the invention as claimed.

Accordingly, the present invention provides for the sterilization of objects using ultraviolet light and non-liquid exposure to ultrasonic waves. The simultaneous emission of ultrasound and ultraviolet light complement each other and can effectively sterilize either organic or inorganic items in a non-liquid environment. This simultaneous combination of ultraviolet light and ultrasonic waves provides for effective sterilization of items without having to place the item in a water or other liquid solution during exposure to the ultrasonic waves. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A method for sterilizing an organic or inorganic object, comprising simultaneously exposing said object to ultrasonic waves and ultraviolet light in a non-liquid environment, wherein said ultraviolet light has a wavelength between approximately 180 nm and approximately 325 nm and a power density ranging from approximately 400,000 microwatts per $cm^2$ per second to approximately 1,000,000 microwatts per $cm^2$ per second, and wherein said ultrasonic waves have a frequency range between approximately 20 KHz and approximately 40 KHz and an output level of approximately 119 dB at approximately 0.5 meters from said object with a maximum power output of approximately 5 watts.

2. A method as recited in claim 1, wherein said ultraviolet light has a wavelength of approximately 254.7 nm.

3. A method as recited in claim 1, wherein said ultrasonic waves have a frequency range between approximately 23 KHz and approximately 25 KHz.

4. A method as recited in claim 1, wherein said ultrasonic waves have a frequency of approximately 24.7 KHz.

5. A method as recited in claim 1, wherein said ultrasound sweeps within said frequency range with a sawtooth pattern having a cycle period of approximately one second.

6. An apparatus for sterilizing an organic or inorganic object, comprising:

(a) an ultraviolet light energy source capable of emitting ultraviolet light at a wavelength between approximately 180 nm and approximately 325 nm and at a power density between approximately 400,000 microwatts per $cm^2$ per second and approximately 1,000,000 microwatts per $cm^2$ per second; and (b) an ultrasound source capable of emitting ultrasound waves at a frequency between approximately 20 KHz and approximately 40 KHz and at an output level of approximately 119 dB at approximately 0.5 meters from said object with a maximum power output of approximately 5 watts;

(c) wherein said ultraviolet light source and said ultrasound source operate simultaneously, and wherein said apparatus is configured for exposing said object to said ultraviolet light source and said ultrasound source in a non-aqueous environment.

7. An apparatus as recited in claim 6, wherein said ultraviolet light has a wavelength of approximately 254.7 nm.

8. An apparatus as recited in claim 6, wherein said ultrasonic waves have a frequency range between approximately 23 KHz and approximately 25 KHz.

9. An apparatus as recited in claim 6, wherein said ultrasonic waves have a frequency of approximately 24.7 KHz.

10. An apparatus as recited in claim 9, wherein said ultrasound source sweeps within said frequency range with a sawtooth pattern having a cycle period of approximately one second.

\* \* \* \* \*